ns Patent [19]

Kidman et al.

[11] Patent Number: 5,316,943
[45] Date of Patent: May 31, 1994

[54] RACEMIC CONVERSION OF USING A TRANSAMINASE

[76] Inventors: Gene E. Kidman, 2172 Pierce St., Ubly, Mich. 48475; Larry E. Robinson, 126 Midway La., Vernon Hills, Ill. 60061; Mark P. Scollar, 620 Oriole La., Mt. Prospect, Ill. 60056; Ian G. Fotheringham, 1606 Brittany Ct., Wheeling, Ill. 60090

[21] Appl. No.: 368,480

[22] Filed: Jun. 19, 1989

Related U.S. Application Data

[63] Continuation-in-part of Ser. No. 206,622, Jun. 14, 1988, abandoned.

[51] Int. Cl.⁵ .................................................. C12P 13/04
[52] U.S. Cl. .................................. 435/280; 435/106; 435/108; 435/110; 435/116; 435/115

[58] Field of Search .............. 435/106, 108, 110, 115, 435/116, 172.3, 280, 849, 252.33, 320

[56] References Cited

U.S. PATENT DOCUMENTS 4,518,692  5/1985  Rozzell .................................. 435/116
4,745,061  5/1988  Aretz et al. ........................... 435/106

Primary Examiner—Sam Rosen
Attorney, Agent, or Firm—John M. Sanders

[57] ABSTRACT

Recombinant cells and an improved method utilizing them is disclosed for the preparation of an optically pure, L-amino acid from its D and D,L isomer forms. The process utilizes cell cultures that possess high aminotransferase activity that exhibits moderate selectivity in the conversion of D and L amino acids to their respective 2-keto acids as well as absolute stereospecificity in the conversion of the 2-keto acids to the L isomer alone.

20 Claims, 4 Drawing Sheets

Figure 4.

Sequence of mutant *tyrB* gene on pIF203

Wild type enzyme

| | | | | | | | | | | | |
|---|---|---|---|---|---|---|---|---|---|---|---|
| Res No: | 29 | 30 | 31 | 32 | 33 | 34 | 35 | 36 | 37 | 38 | 39 |
| Residue: | Val | Asn | Leu | Ser | Ile | Gly | Leu | Tyr | Tyr | Asn | Glu |
| DNA code: | GTG | AAT | TTA | AGT | ATC | GGT | CTG | TAC | TAC | AAC | GAA |

*tyrB* gene with *EcoRI* and *AccI* sites generated Residues 31 and 36 altered

| | | | | | | | | | | | |
|---|---|---|---|---|---|---|---|---|---|---|---|
| Sequence on pIF200: | 29 | 30 | 31 | 32 | 33 | 34 | 35 | 36 | 37 | 38 | 39 |
| | Val | Asn | Ser | Ser | Ile | Gly | Leu | Val | Tyr | Asn | Glu |
| | GTG | AAT | TCA | AGT | ATC | GGT | CTG | GTC | TAC | AAC | GAA |

Mutated bases

*tyrB* mutant altered at residue 35 with reversion of mutations at residues 31 & 36

| | | | | | | | | | | | |
|---|---|---|---|---|---|---|---|---|---|---|---|
| Sequence on pIF203: | 29 | 30 | 31 | 32 | 33 | 34 | 35 | 36 | 37 | 38 | 39 |
| | Val | Asn | Leu | Ser | Ile | Gly | Val | Tyr | Tyr | Asn | Glu |
| | GTG | AAT | TTA | AGT | ATC | GGT | GTG | TAC | TAC | AAC | GAA |

Mutated base

Reversion of mutations present in pIF200 generates the mutant *tyrB* gene in which only residue 35 is altered, from CTG (Leu) to GTG (Val)

RACEMIC CONVERSION OF USING A TRANSAMINASE

RELATED APPLICATIONS

This patent application is a Continuation-in-Part of U.S. Ser. No. 07/206,622 entitled: Racemic Conversion of D, L Amino Acids Using a Cultured Transaminase, filed on Jun. 14, 1988 now abandoned.

BACKGROUND OF THE INVENTION

It is well recognized that all amino acids exist in one of two isomer forms, known as the L-form and its mirror image, the D-form. The aromatic amino acid phenylalanine, for example, has two optically active enantiomers, L-phenylalanine and D-phenylalanine. In its major application, a component of aspartame the popular low calorie sweetener, it is preferred to separate the two isomers or convert a racemic mixture of the two to obtain one of the enantiomers that is relatively free of contamination by the other. Aspartame itself is a dipeptide comprised of two amino acids, aspartic acid and phenylalanine. It has been known for quite some time that the sweetening property of the dipeptide is dependent upon the stereochemistry of these individual amino acids.

Since both of these amino acids can exist in either the D (dextro) or L (levo) form, it has been determined that L-aspartyl-L-phenylalanine esters are sweet while the corresponding D-D, D-L and L-D isomers are not. Combinations of the isomers which contain the L-L dipeptide, DL-aspartyl-L-phenylalanine, L-aspartyl DL-phenylalanine and DL-aspartyl-DL-phenylalanine are sweet, but only half as sweet since the racemate contains ½ of the L-L moiety. Hence, in the manufacture of aspartame, it is most desirable to have a starting material of phenylalanine that is comprised of purely the L-isomer form.

Phenylalanine is conventionally made either through chemical synthesis, enzymatic synthesis or fermentation. Most of these methods result in a racemic mixture of the D and L isomers which must either be separated or resolved, to yield a pure L-phenylalanine fraction. Ideally, a method or process whereby the D isomers could be converted to the L isomer would not only do away with the need for the additional and costly separation or resolution steps, but it would also increase the final yield of the desired product.

Biocatalytic processes resulting in the formation of a specific isomer are known in the art. For example, L-phenylalanine can be produced via enzymatic synthesis from cinnamic acid and ammonia using the enzyme phenylalanine-ammonia lyase. L-alanine may also be produced in a pure fraction by the enzymatic decarboxylation of L-aspartic acid. See U.S. Pat. Nos. 3,458,400 and 3,463,704. Wood et al., U.S. Pat. No. 4,600,692 also utilized transaminases in the preparation of L-phenylalanine and oxaloacetate from phenylpyruvic acid, pyridoxal-5-phosphate and an amine donor such as L-glutamate or L-aspartate in a reversible reaction.

Of particular interest is Rozzell, J., U.S. Pat. No. 4,518,692. A process is disclosed therein whereby L-amino acids are produced by transamination. The process comprises reacting an alpha-keto acid or a racemic mixture of an amino acid with L-aspartic acid in the presence of a transaminase enzyme to produce an alpha amino acid corresponding to the alpha keto-acid and oxaloacetate which must be subsequently decarboxylated. The transamination reaction requires a multi-enzyme system comprising the addition of oxaloacetate decarboxylase, D-amino acid oxidase and pyridoxal-5-phosphate which are not needed in the process of the present invention. D-amino acid oxidase is a mammalian enzyme extracted from hog kidney. A byproduct of this reaction is hydrogen peroxide which has been shown to inactivate enzymes and can cause decomposition of 2-ketoacids. The enzyme is also expensive and thereby increases the cost of the overall process.

Also of interest to the background of the present invention is U.S. Pat. No. 4,745,061 to Aretz et al. which discloses a D-amino acid transaminase that has been isolated from *Bacillus licheniformis*. The enzyme is shown to be useful in the preparation of D-amino acids from Δ keto acids and is suitable for resolving racemates of D,L amino acids by converting the D-amino acid to its corresponding α-keto acid which is then separated. The recovery of pure L-amino acid would thus require costly purification and separation steps not necessary in the practice of the present invention.

It is an object of the present invention to provide a process for the production of L-amino acids using a transaminase that is stereospecific in the synthesis of L-amino acids. More specifically, it is an object of the present invention to provide a process for the production of optically pure L-phenylalanine from a D, L racemic mixture using a transaminase from a culture without the required addition of aspartate, D-amino acid oxidase, oxaloacetate decarboxylase or catalase.

SUMMARY OF THE INVENTION

The present invention provides an enzymatic or microbial bioconversion process that is capable of producing L-amino acids from the corresponding racemic mixture or from purely D-amino acid sources. The invention utilizes a transaminase that is moderately selective in the conversion of D and L amino acids to 2-keto acids, but exhibits absolute stereospecificity in the conversion of 2-keto acids to L-amino acids. Hence, a D amino acid or a D, L mixture of an amino acid can react with a) glucose and ammonia or b) aspartic acid in the presence of a transaminase to produce the corresponding L-amino acid and c) carbon dioxide or d) oxaloacetate.

BRIEF DESCRIPTION OF THE DRAWINGS

4. FIG. 4 is a schematic representation of the gene sequence for the mutant tyrB gene as found on pIF203 and its respective amino acid sequence for the mutant enzyme encoded thereby as compared to the same for the wild type tyrB gene.

DETAILED DESCRIPTION OF THE INVENTION

Cells possessing a high degree of transaminase activity are cultured and the mixture of the D and L isomers of the amino acid of interest is made to come into contact with these cells either in a fermenter or through an immobilized cell culture. The cells are able to convert either the D or L form of the desired amino acid to its respective 2-keto acid. It has been found that what in fact occurs is that a reaction equilibrium is set up as follows:

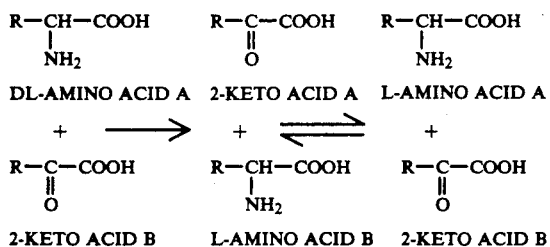

The advantage of creating this equilibrium within a transaminase containing cell culture is that the transaminase is only moderately selective in the conversion of D and L isomers to their respective 2-keto acids, but exhibit absolute stereospecificity in the reverse conversion of the 2-keto acid to only its L isomer form. Consequently, the first step of the above reaction is irreversible with respect to the D isomer of the amino acid.

Transaminases are synthesized in the metabolic pathways of many species of bacteria, but have been found to be particularly of value in *Escherichia coli* which can be genetically engineered to overproduce the enzyme and hence increase the reaction rate described previously herein.

In *E. coli*, there are essentially aminotransferases that catalyze the terminal steps in amino acid biosynthesis. The aromatic aminotransferase is the product of the tyrB gene (tyrosine aminotransferase) and is active in the synthesis of phenylalanine, tyrosine, aspartate and leucine. Aspartate aminotransferase, regulated by the aspC gene, is active in the synthesis of aspartate, tyrosine and phenylalanine. The branched-chain aminotransferase which is a product of the ilvE gene is active in the synthesis of leucine, isoleucine, valine and in vivo, phenylalanine. A fourth aminotransferase, transaminase C has been isolated, but not well characterized.

Strains of *E. coli* K-12 are cultured on minimal plates and grown at 370° C. for 16 hours. Strains found useful in the present application are described in detail by Fotheringham et al. (1986), J. Biochem 234, 593–604 which is incorporated by reference herein. The HW857 host strain is essentially a wild type *E. coli* K-12 wherein the host chromosome genes responsible for aminotransferase activity have been mutated or deleted using standard cell techniques resulting in tyrB (tyrosine aminotransferase) and aspC (aspartate aminotransferase) deficient cells.

Figure 1:
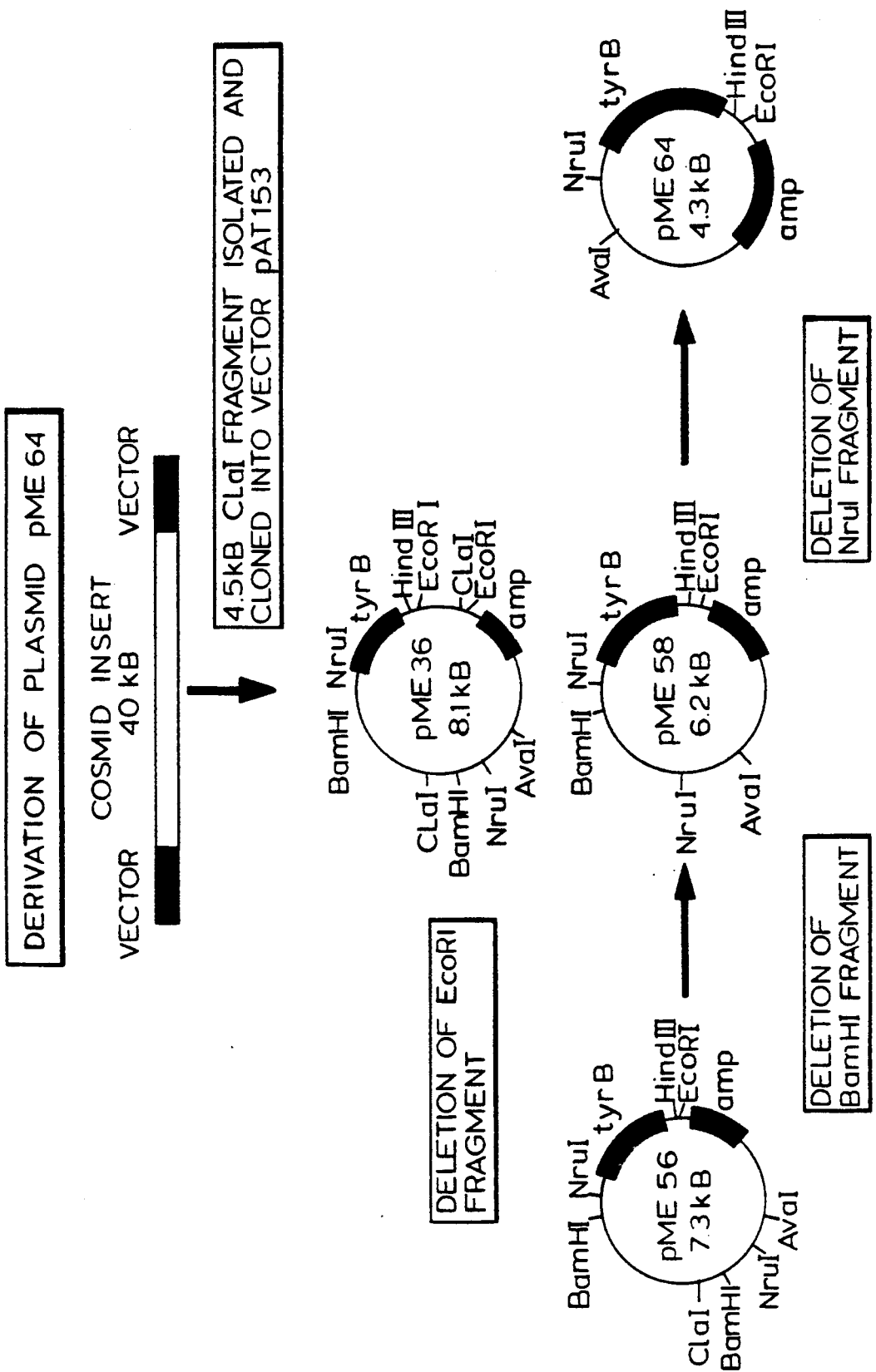
FIG. 1 is a schematic representation of the derivation of plasmid pME64 containing the wild type tyrB gene.

This transaminase deficent bacteria serves as the host microorganism to three plasmids which can be introduced into the host by standard conjugation, transduction or transformation cell techniques. Plasmid pME64 is constructed so that the tyrB wild type enzyme is expressed (see FIG. 1). This plasmid carries the tyrB gene. It was created by deletion of an NruI fragment from pME58. Originally the wild type tyrB gene was isolated from a cosmid gene bank derived from the chromosome of *E. coli* K12. This clone was cleaved with ClaI and a 4.5kB fragment containing the tyrB gene was isolated. This was cloned into the vector pAT153 giving pME38.

pME38 was then cleaved with EcoRI thereby deleting a fragment and leaving a smaller tyrB insert. This plasmid was designated pME56. pME56 was cleaved with BamHI thereby deleting a further fragment and leaving a yet smaller tyrB insert. This plasmid was designated pME58. pME58 was subsequently cleaved with NruI generating the final deletion to leave the smallest tyrB insert. This plasmid is pME64.

Figure 2:
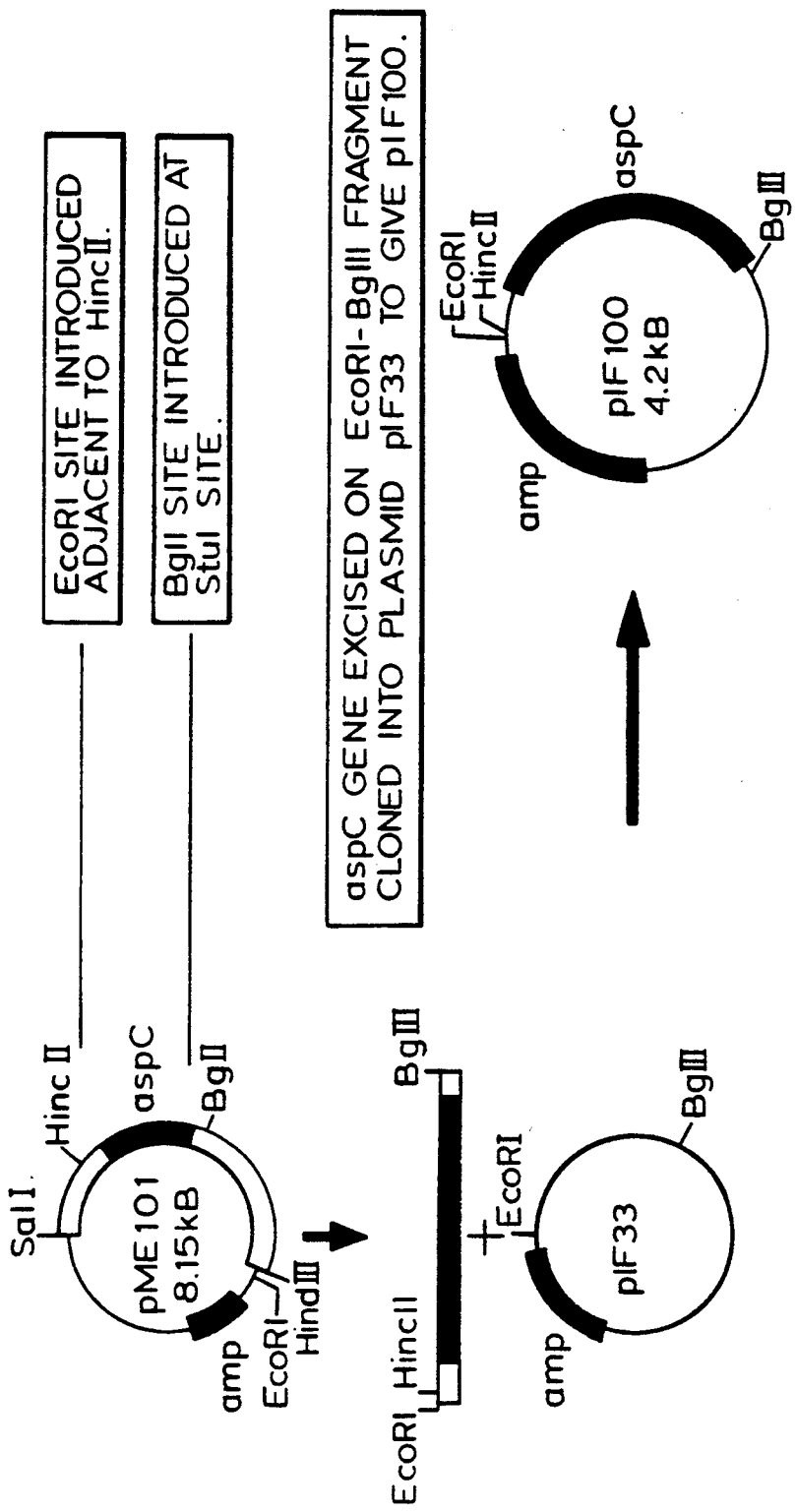
FIG. 2 is a schematic representation of the derivation of plasmid pIF100 containing the aspC wild type gene.

Plasmid pIF100 is constructed so that the aspC wild type enzyme is expressed (see FIG. 2). It was created following determination of the nucleotide sequence of the aspC gene and its flanking regions on plasmid pME101. Sequence information showed the aspC gene to be flanked by an upstream site for HincII and a downstream site for StuI. A small DNA linker incorporating a BglII site was then inserted at the StuI site to facilitate manipulation. An EcoRI site was then introduced adjacent to the HincII site. The aspC gene was then cloned on the EcoRI to BglII fragment into the similarly cleaved plasmid vector pIF33. In this vector, the single AvaI site had been removed and a BglII linker had been inserted at the NruI site. Insertion of the aspC fragment generated plasmid pIF100.

Figure 3:
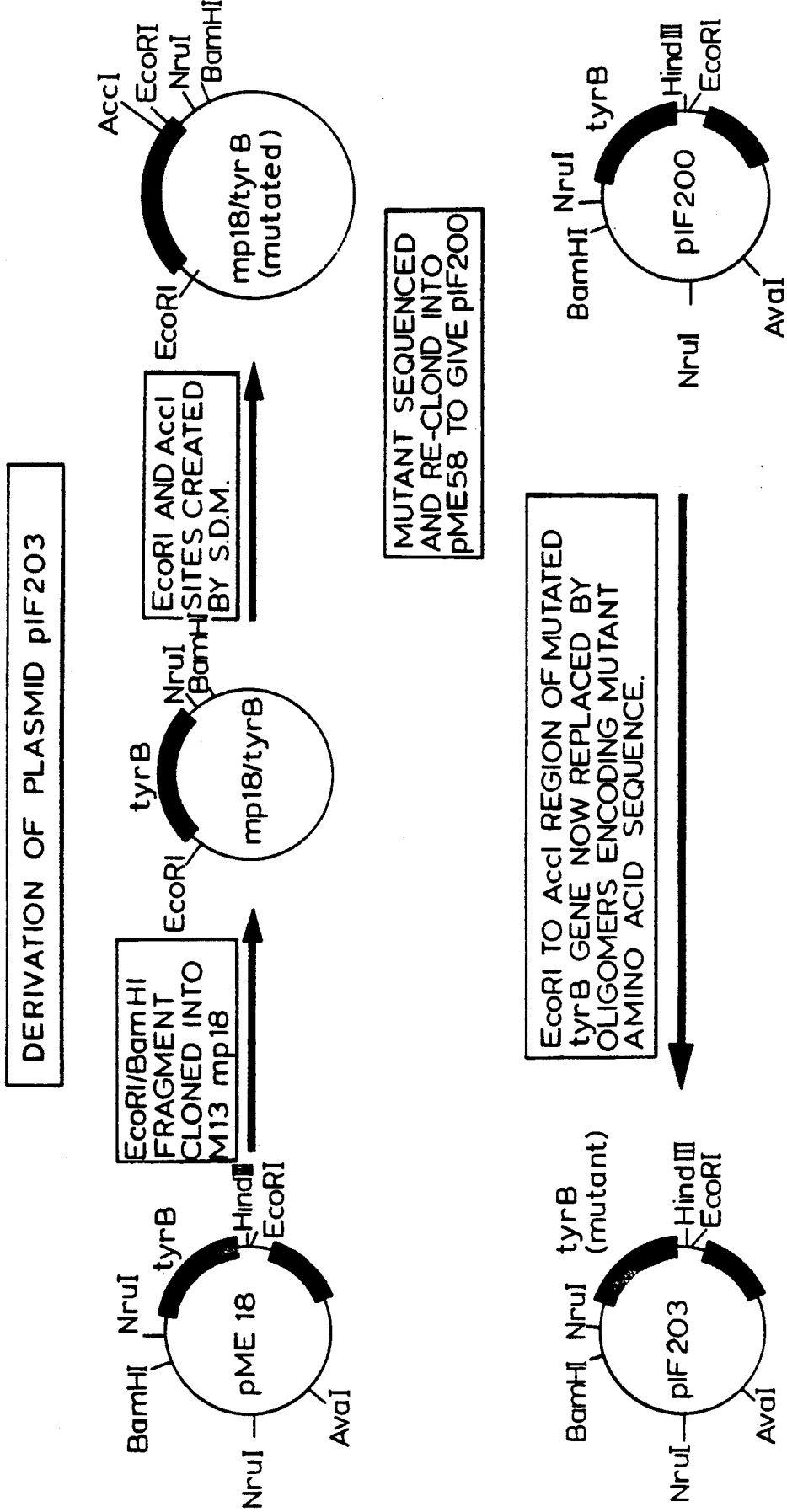
FIG. 3 is a schematic representation of the derivation of plasmid pIF203 containing a mutant tyrB gene.

Plasmid pIF203 is constructed so that a mutant transaminase tyrB enzyme is expressed (see FIG. 3). Plasmid pIF203 carries a derivative of the tyrB gene which was created by site-directed mutagenesis. This mutant encodes an enzyme altered such that codon 35 now reads GTG, encoding valine as opposed to CTG which encodes leucine in the wild type enzyme. To construct this mutant, two restriction enzyme sites were introduced within the tyrB gene using two independent DNA oligonucleotides in separate experiments. These sites were for the enzymes EcoRI and AccI. Site-directed mutagenesis was carried out on the EcoRI to BamHI fragment of pME58 containing the tyrB gene cloned into the EcoRI to BamHI region of phage M13 mpl8. Following mutagenesis the fragment was sequenced to confirm the mutations and then cloned back into pME58 by AccI and partial EcoRI cleavage. The two sites lie 19bp apart and this enabled the removal of the intervening region of DNA following cleavage with these enzymes. The intervening DNA sequence was then replaced by a double stranded region of DNA comprising two synthetic oligonucleotide linkers. This fragment restored the original sequence at the two mutated sites and in addition enabled a further single base change in the intervening region of C to G in codon 35. The resulting mutant thereby contained only a single base alteration in which the CTG (leucine) codon at position 35 in the amino acid sequence became GTG (valine) (see FIG. 4).

These species were used in the preferred embodiment of the present invention although any transaminase producing cell may be cultured and used within the scope of the present invention and tailored to the particular amino acid desired by insertion of the appropriate plasmids.

It is preferred, however, that one of the host strains transformed with one of the respective plasmids is inoculated into 50 ml. flasks and cultured on a medium comprised of the following:

| | |
|---|---|
| K$_2$HPO$_4$ | 7.5 g/l |
| (NH$_4$)$_2$HPO$_4$ | 10.0 g/l |
| MgSO$_4$ × 7 H$_2$O | 1.5 g/l |
| Ferric ammonium citrate | 0.24 g/l |
| Yeast Extract | 0.1 g/l |

| | |
|---|---|
| -continued | |
| Glucose | 20.0 g/l |

The pH of the medium is adjusted to 7.2 before sterilization. The cells are cultured at approximately 37° C., preferably for 16 hours, in order to insure sufficient intracellular transaminase production. Transaminases with varying selectivities are useful with respect to the conditions employed and/or amino acid to be synthesized and may be expressed from a gene either located chromosomally or on a plasmid incorporated within a number of cell cultures described in Umbarger, H., Annual Rev. Biochem., 47 pp. 533–606 (1978) which is herein incorporated by reference. The cells can then either be further harvested into a suitable fermenter type vessel or immobilized in a gel matrix for the D, L isomer conversion.

Generally, the conversion is run at a temperature which is maintained at approximately 26°–40° C., preferably 32°–37° C. A pH range of 6.8 to 7.4, preferably 7.0–72., is also one that will assure the greatest rate of conversion. After a suitable period of time, the D-phenylalanine present in the reaction broth will be reduced to 6% or less, and may be harvested from the fermenter. This last portion is difficult to convert to the L isomer since the transaminase affinity for the substrate is reduced. Complete conversion of the D to the L isomer form is achieved by running the reaction conversion with an excess amount of transaminase in the culture system.

The following examples are set forth to better teach and illustrate the concept of the present invention. They are to define the practice of the invention and by no means are intended as limiting its spirit or scope as defined by the claims.

EXAMPLE I

Preparation of L-Phenylalanine

To flasks containing strains of *E. coli* K-12 that were modified with the aforementioned plasmids is added 50 ml of a solution of the following concentrations:

| | |
|---|---|
| (1) D-Phenylalanine | 10.0 g/l |
| (2) DL-phenylalanine | 10.0 g/l |

The pH of these solutions is adjusted to 7.2 before sterilization. Glucose and NH4OH are added at intervals as needed to maintain the pH and an adequate supply of glucose. The ratios of the L and D isomers existing after the transaminase reaction was run were determined using HPLC analysis after derivatization with Marfey's reagent. See Marfey, P., Carlsberg Res. Commun. 49 591–596 (1984); also for HPLC analysis conditions see Pierce Chemicals 1988 Handbook, p. 131.

The conversion rates of the racemic mixtures were found to be as follows:

1) A reaction mixture containing 10 g/l D-phenylalanine when mixed with a cell culture of HW857 pIF100 was found to be 90% converted to L-phenylalanine after 52 hours.

2) A reaction mixture containing 10.0 g/l D,L-phenylalanine when mixed with a cell culture of HW857 pIF100 was found to be 90% converted to L-phenylalanine after 31 hours.

3) A reaction mixture containing 10.0 g/l D,L phenylalanine when mixed with a cell culture of HW857 pMe64 was found to be 98% converted to L-phenylalanine after 43 hours.

4) A reaction mixture containing 10.0 g/l D,L-phenylalanine when mixed with a cell culture of HW857 pIF203 was found to be 78% converted to L-phenylalanine after 29 hours.

EXAMPLE II

Preparation of L-Leucine

The conversion is carried out as described in Example 1 above wherein 50 ml. of a solution of either (1) D- or (2) D,L-leucine is added in the following concentrations.

| | |
|---|---|
| (1) D-leucine | 20.0 g/l |
| (2) DL-leucine | 10.0 g/l |

(1) A reaction mixture containing 20 g/l D-leucine when mixed with a cell culture of HW857 pME64 was found to be 27% converted to pure L-leucine after 28 hours.

2) A reaction mixture containing 20 g/l D-leucine when mixed with a cell culture of HW857 pIF203 was found to be 20% converted to pure L-leucine after 28 hours.

3) A reaction mixture containing 10 g/l D,L-leucine when mixed with a cell culture of HW857 pME64 was found to be 78% converted to pure L-leucine after 28 hours.

EXAMPLE III

Preparation of L-2-Amino-3-Phenyl Butanoic Acid

To a flask containing *E. coli* (HW857 pME64) with the pH adjusted to 7.2 as in Example 1 above is added 50 ml of a solution of D, L-2-amino-3-phenyl butanoic acid (4.0 g/l). Glucose and NH4OH are added at intervals necessary to supply a proper energy source and to maintain the pH at 7.2 After 28 hours, 47% of the D,L isomer was converted to L-2-amino-3-phenyl butanoic acid.

EXAMPLE IV

Preparation of L-Homophenylalanine

To a flask containing *E. coli* (HW857 pME64) with the pH readjusted to 7.2 is added 50 ml of a solution of DL-homophenylalanine (0.18 g/1). Glucose and NH4OH are added at intervals as needed to maintain the pH at about 7.2 and an adequate supply of glucose. After a period of 24 hours the reaction mixture contained 81% L-homophenylalanine.

EXAMPLE V

Purified transaminase was used to demonstrate the discovery that transaminase is only moderately selective in the deamination step to form 2-keto acids from D,L amino acids.

The enzyme assay mixture was comprised as follows:
1) 18.8 mM/l. a-ketoglutarate
2) 190 mM/l. pyridoxal-5-phosphate
3)
 a) 0.1-12.0 mM/l. D-phenylalanine or
 b) 0.1-12.0 mM/1 L-phenylalanine.

3.2 ml potassium phosphate buffer (0.5m) at pH 7.2 is equilibrated at 37° C. for five minutes. Then 0.1 ml of enzyme solution (tyrosine aminotransferase or aspartate aminotransferase) containing between 0.03 to 0.05 units are added and the reaction mixture is incubated for five minutes at 37° C. The reaction is stopped by the addition of 0.2 ml of 10N NaOH and the 2-keto acid (phenylpyruvic acid) produced is measured spectrophotometrically at 320 nm.

The inverse reaction rates and substrate concentrations are plotted in Lineweaver-Burke coordinates and the following kinetic constants are obtained by curve fitting.

| Summary of Kinetic Parameters | | | | |
|---|---|---|---|---|
| Enzyme protein | 1) $K_m$, millimoles/liter | | 2) $V_{max}$, micromoles/ min × mg | |
| | D-Phe | L-Phe | D-Phe | L-Phe |
| TAT | 21.6 | 1.13 | 56.0 | 242.0 |
| AAT | 20.0 | 3.6 | 8.0 | 20.8 |

TAT = tyrB gene product, tyrosine aminotransferase
AAT = aspC gene product, aspartate aminotransferase As is made clear in column 1 above, the affinity of both enzymes for D-phenylalanine is much lower than their affinities for L-phenylalanine. This is to be expected. On the other hand, the data from column 2 shows unexpectedly the fact that both enzymes exhibit high activity with respect to D-phenylalanine as well as L-phenylalanine. Hence, on a comparative basis, both enzymes activities are not proportional with respect to their affinities for their respective substrates. This is further evidence that the enzymes are only moderately selective in the conversion of D and L isomers to their respective 2-keto acids.

What we claim is:

1. A method for the production of an optically pure L-amino acid from a D,L racemic mixture of the amino acid comprising the steps of:
   i) treating the racemic mixture of the amino acid with a transaminase-producing microorganism;
   ii) fermenting said racemic mixture of the amino acid and microorganism at a suitable temperature and pH for a suitable period of time; and
   iii) recovering said optically pure L-amino acid.

2. The method of claim 1 wherein said transaminase is derived from *Escherichia coli*.

3. The method of claim 2 wherein said transaminase is stereospecific for the conversion of a D-amino acid to its L form.

4. The method of claim 3 wherein said transaminase is present in whole cells.

5. The method of claim 4 wherein said cells are cultured in a fermenter.

6. The method of claim 5 wherein said D,L racemic mixture of the amino acid is selected from the group comprising D,L-phenylalanine, D,L-2-amino-3-phenyl butanoic acid, D,L-homophenylalanine, D,L-glutamic acid, D,L-tryptophan, D,L-leucine, D,L-isoleucine, D,L-tyrosine and D,L-valine.

7. The method of claim 6 wherein said transaminase is selected from the group consisting of tyrosine aminotransferase, aspartate aminotransferase, and isoleucine transaminase.

8. The method of claim 7 wherein said aminotransferase is under plasmid control.

9. The method of claim 8 wherein said plasmid is selected from the group consisting of pME64, pIF100, and pIF203.

10. A method for the production of an optically pure L-amino acid from a D,L racemic mixture of the amino acid comprising:
    i) adding said racemic mixture of the amino acid to a culture of transaminase-producing microorganisms;
    ii) fermenting said culture and racemic mixture of the amino acid at an appropriate pH and temperature for a suitable period of time and,
    iii) recovering said optically pure L-amino acid.

11. The method of claim 10 wherein said D,L racemic mixture of the amino acid is selected from the group consisting of D,L-phenylalanine, D,L-2-amino-3-phenyl butanoic acid, D,L-homophenylalanine, D,L-aspartic acid, D,L-glutamic acid, D,L-leucine, D,L-isoleucine, D,L-valine, D,L-tyrosine and D,L-tryptophan.

12. The method of claim 11 wherein said transaminase is selected from the group consisting of tyrosine aminotransferase, aspartate aminotransferase and isoleucine aminotransferase.

13. The method of claim 12 wherein said aminotransferase is under plasmid control.

14. The method of claim 13 wherein said plasmid is selected from the group consisting of pME64, pIF100, and pIF203.

15. The method of claim 14 wherein said fermentation is run at a temperature of approximately 26°-40° C.

16. The method of claim 15 wherein said fermentation is run at a pH of approximately 6.8-7.4.

17. The method of claim 16 wherein said transaminase producing microorganism is *Escherichia coli*.

18. The method of claim 17 wherein said transaminase producing microorganism is cultured in a fermenter.

19. The method of claim 18 wherein said D,L racemic amino acid mixture is added to a fermenter of transaminase producing microorganisms to yield a substantially optically pure amino acid.

20. The method of claim 18 wherein said optically pure amino acid is selected from the group consisting of L-phenylalanine, L-leucine, L-glutamic acid, L-isoleucine, L-valine, L-aspartic acid, L-2-amino-3-phenyl butanoic acid, L-homophenylalanine, L-tyrosine and L-tryptophan.

* * * * *